United States Patent [19]

Rezaian

[11] 4,401,112

[45] Aug. 30, 1983

[54] SPINAL FIXATOR

[76] Inventor: Seyed M. Rezaian, The Hotel Isola Garni, Niesenweg 10, CH 3012 Bern, Switzerland

[21] Appl. No.: 308,016

[22] Filed: Oct. 2, 1981

[51] Int. Cl.³ .......................... A61F 5/04; A61B 17/18

[52] U.S. Cl. ............................... 128/92 B; 128/84 R; 128/92 C; 128/92 E; 3/1.91

[58] Field of Search ................. 128/92 R, 92 B, 92 C, 128/92 D, 92 E, 84 R, 92 G, 69, 75, 78; 3/1.9, 1.91

[56] References Cited

U.S. PATENT DOCUMENTS

| | | | |
|---|---|---|---|
| 3,741,205 | 6/1973 | Markolf et al | 128/92 D X |
| 4,289,123 | 9/1981 | Dunn | 128/92 B X |
| 4,309,777 | 1/1982 | Patil | 128/92 C X |

FOREIGN PATENT DOCUMENTS

| | | | |
|---|---|---|---|
| 1051847 | 9/1953 | France | 128/92 D |
| 1243353 | 8/1971 | United Kingdom . | |

OTHER PUBLICATIONS

"Knodt Distraction-Fusion Instrumentation" Product Encyclopedia, Zimmer-USA, Inc., 1978, pp. B203 and B204.

*Primary Examiner*—Ronald L. Frinks
*Attorney, Agent, or Firm*—William D. Hall

[57] ABSTRACT

A spinal fixator is in the form of a turnbuckle the end sections of which terminate as circular flat plates formed with upwardly and downwardly protruding spikes for engaging in the bone of respective vertebrae above and below a broken vertebra. Following decompression of the spinal cord, the fixator is inserted and extended to engage the spikes in the respective vertebrae and thereafter holds the spinal cord decompressed.

14 Claims, 4 Drawing Figures

SPINAL FIXATOR

BACKGROUND OF THE INVENTION

1. Field of the Invention

This invention relates to a spinal fixator.

2. Description of the Prior Art

Surgical treatment for fracture of the spine has been known for very many years. However, various techniques have been used, with varying degrees of success.

It would appear that laminectomy is of no benefit in the management of spinal cord injury.

A simple plating and screw technique is known involving fixation on the spinal process, but, particularly where the spinal process is broken, does not prevent redislocation.

In recent years, spring stabilization, plate and screws fixation into the pedicle, and external fixation have all been tried.

It has become more widely accepted nowadays that stability of the spine materially affects the ability of the injured neural tissue to heal. Furthermore, commonly in spinal injury the cord will swell owing to biochemical change and, in the limited space of the canal, become squeezed. Moreover, a disc and ligaments are often ruptured and the cord compressed anteriorly. Therefore, in good management of spinal injury, not only stability of the spine but also decompression of the cord anteriorly are to be sought after.

SUMMARY OF THE INVENTION

According to the present invention, there is provided a spinal fixator, comprising first and second means having respective bearing portions for bearing against respective vertebral portions respectively above and below a broken verebral portion and movable relative to each other, and adjusting means arranged to adjust the distance between said bearing portions for thereby setting the distance between said respective vertebral portions.

Owing to the invention, it is possible to achieve a high degree of stabilization of the spine and reliably to maintain decompression of the cord.

The fixator can replace the whole or part of a broken vertebra.

BRIEF DESCRIPTION OF THE DRAWINGS

In order that the invention may be clearly understood and readily carried into effect, reference will now be made, by way of example, to the accompanying drawings, in which.

Figure 3:
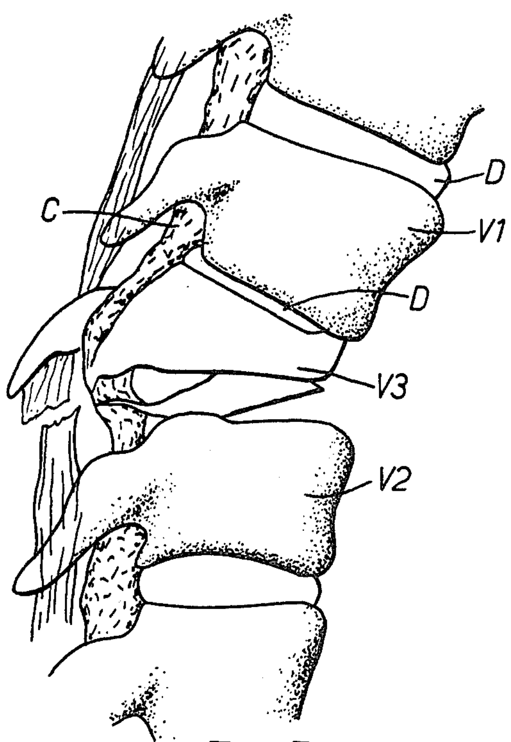
FIG. 3 shows a perspective view of a broken spine.

Commonly, in fracture of the spine, one or more discs D and ligaments are ruptured and the spinal cord C is compressed anteriorly, as shown in FIG. 3. Moreover, owing to biochemical change, the cord swells and, in the limited space of the canal, therefore becomes squeezed. It would therefore appear that, for correct management of spinal injury, not only is stabilization of the spine highly desirable, but also decompression of the cord C anteriorly is highly desirable.

Figure 1:
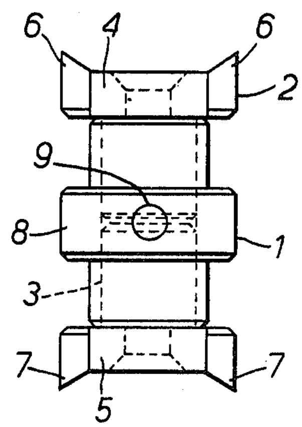
FIG. 1 shows a side elevation of an internal spinal fixator.
Figure 2:
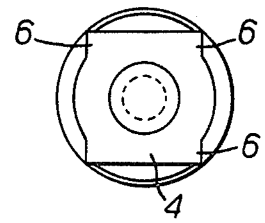
FIG. 2 shows a plan view thereof.

Referring to FIGS. 1 and 2 the fixator is in the form of a turnbuckle. In practice, it is made of high quality stainless steel in three differing sizes. It consists of a rigid internally threaded intermediate section 1 and upper and lower externally threaded end sections 2 and 3. The end sections 2 and 3 of course have their external threadings of opposite hand. Moreover, the sections 2 and 3 terminate as flat plates 4 and 5, respectively, formed with respectively upwardly and downwardly protruding spikes 6 and 7, two for each plate. The middle 8 of the intermediate section 1 is of enlarged cross-section externally and is formed with two threaded holes 9 for receiving a tommy bar. By turning of the intermediate section 1 relative to the end sections 2 and 3, the turnbuckle can be extended by about half its length from its condition of minimum extension.

Figure 4:
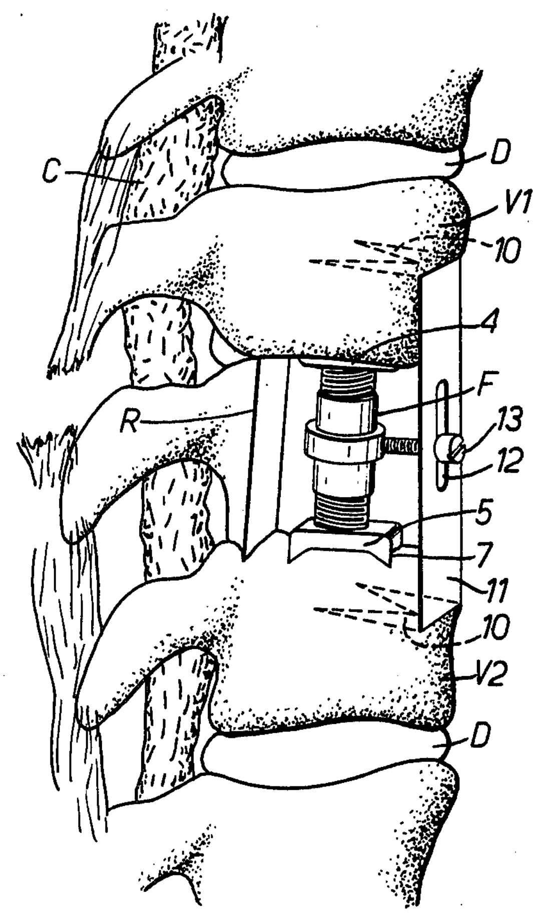
FIG. 4 shows a perspective view of the fixator in use in the spine.

The use of the fixator will now be described with reference to FIGS. 3 and 4.

Through a standard antero-lateral approach, the spinal facture is exposed. Any ruptured disc, ruptured ligaments, broken bone fragments, and so on are removed. The spinal cord C is completely decompressed. Between the vertebrae V1 and V2 immediately above and immediately below the broken vertebra V3 is inserted the fixator F. The fixator F is extended until the spikes 6 and 7 are engaged firmly in the bone of the vertebrae V1 and V2, the flat plates 4 and 5 preventing excessive penetration into the bone. It is desirable that there should be inserted in addition to the fixator F a piece of rib R for biological bridging of the vertebra V3.

Even more reliable stabilization can be achieved by driving into the vertebrae V1 and V2 the respective sharp forked ends 10 of a sheet metal staple 11 formed with a central vertical slot 12 which receives the shank, but not the head, of a bolt 3 which is screwed into one of the threaded holes 9. The staple 11 not only connects the vertebrae VI and V2 more stably together but the bolt 13 prevents rotation of the section 1 relative to the sections 2 and 3.

The fixator described above can be used with safety to immobilise securely the spine to facilitate nursing and rehabilitation procedures. It also decompresses the spinal cord to give the cord the maximum chance of recovery from any damage.

Use of the fixator described has a great advantage in that patients can be discharged from hospital between two and four weeks from the fixation operation, even if prior to the operation they were paralyzed in both legs owing to the compression of the spinal cord.

I claim:

1. A spinal fixator, comprising:

first and second means having respective bearing portions for bearing against respective vertebral portions respectively above and below a broken vertebral portion and movable relative to each other, adjusting means arranged to adjust the distance between said bearing portions for thereby setting the distance between said respective vertebral portions, wherein said first and second means and said adjusting means are provided by upper and lower and intermediate sections, respectively, of a turnbuckle, and a staple for bridging said respective vertebral portions, and connecting means for connecting said staple to said intermediate section to prevent rotation of said intermediate section relative to said upper and lower sections and said staple.

2. A device according to claim 1, wherein said intermediate section is formed with approximately radial threaded holes for receiving a tommy bar, said connecting means comprises an externally threaded elongate element for screwing into one of the threaded holes, and said staple is formed with an aperture therethrough for closely receiving said element.

3. A device according to claim 1 further in which said connecting means is a screw held by said staple and operable to engage the intermediate section of said turnbuckle and prevent that section from rotating.

4. A device according to claim 3 further including a vertical slot in said staple whereby the vertical position of said screw may be varied.

5. A prosthetic spinal fixator for insertion between the lower face of a first vertebra portion and the upper face of a second vertebral portion that is below the first one comprising:

jacking means, composed of material suitable for bone surgery, for insertion directly between said upper and lower faces, said jacking means having an upper end for engaging said lower face and a lower end for engaging said upper face and a rigid intermediate section adjustable to rigidly vary the distance between said upper and lower ends for thereby decompressing the spinal cord and setting the distance between said first and second vertebral portions, said upper and lower ends having spike means for penetrating their complementary faces and each of said ends also having a surface that will be flush with its complementary face over a substantial area, said jacking means also having a height about equal to the height of a vertebral portion.

6. A prosthetic spinal fixator as defined in claim 5 in which said jacking means is a turnbuckle, said intermediate section being rotatable to vary said distance.

7. In a prosthetic spinal fixator as defined in claim 5, said jacking means comprising a turnbuckle which replaces a part of a broken vertebra and is comprised of upper, lower and intermediate sections aligned with the spinal cord in a substantially linear manner of which the upper and lower sections bear upwardly and downwardly against respective vertebral portions respectively above and below a broken vertebral portion and are movable relative to each other, and of which the intermediate section is adjustable to vary the distance between the upper and lower sections for thereby decompressing the spinal cord and setting the distance between said respective vertebral portions.

8. A device according to claim 5, including a U-shaped staple, longer than said jacking means, having means for penetrating the vertical sidewalls of the upper and lower vertebrae portions respectively to attach the staple to said portions.

9. In a device according to claim 8, said staple including means connecting the staple to said jacking means for maintaining the selected height of the jacking means.

10. The method of positioning spaced vertebral portions of the spinal cord, the upper one of the vertebral portions having a lower face, and the lower one of the vertebral portions having an uoper face, comprising:

inserting jacking means wholly within the space that is between said upper and lower faces and adjusting the height of the jacking means to provide decompression of the spinal cord and to also rigidly set the distance between said upper and lower faces.

11. The method of positioning spaced vertebral portions as defined in claim 10 which includes the step of preventing slippage between each end of the jacking means and its complementary vertebral face.

12. The method of positioning spaced vertebral portions as defined in claim 10 which includes effecting penetration of each end of the jack into its complementary face of a vertebral portion, whereby to prevent slippage.

13. The method of positioning spaced vertebral portions as defined in claim 12 which also includes connecting a staple to (a) a vertical side wall of the upper vertebral portion and also (b) a vertical side wall of the lower vertebral portion.

14. The method of positioning spaced vertebral portions as defined in claim 13 which also includes connecting the staple to the jacking means to maintain its position.

* * * * *